United States Patent [19]
Ramachandran et al.

[11] Patent Number: 6,085,584
[45] Date of Patent: Jul. 11, 2000

[54] AUTOMATIC FIBRE TESTING SYSTEM

[75] Inventors: Shekaripuram Narayanaswamy Ramachandran; Varadarajan Srinivasan, both of Coimbatore, India

[73] Assignee: Premier Polytronics Ltd., Coimbatore, India

[21] Appl. No.: 09/074,748

[22] Filed: May 8, 1998

[51] Int. Cl.[7] .................................................. G01N 33/36
[52] U.S. Cl. .................................................. 73/159; 73/160
[58] Field of Search ........................... 73/159, 160, 800, 73/831, 856, 866

[56] References Cited

U.S. PATENT DOCUMENTS

| | | |
|---|---|---|
| 5,167,150 | 12/1992 | Shofner et al. ............................ 73/160 |
| 5,178,007 | 1/1993 | Ghorashi et al. .......................... 73/159 |
| 5,611,238 | 3/1997 | Bader et al. ............................... 73/160 |
| 5,799,103 | 8/1998 | Schneider et al. ........................ 73/160 |
| 5,842,373 | 12/1998 | Stein et al. ................................ 73/160 |

*Primary Examiner*—Hezron Williams
*Assistant Examiner*—Michael Cygan
*Attorney, Agent, or Firm*—Dority & Manning

[57] ABSTRACT

The device for the preparation of fibrous material to be tested comprises means for fastening said fibrous material, means for partitioning the fibrous material, and means for clamping and separating the fibrous material. The means for fastening, the means for partitioning and the means for clamping operate in essentially parallel surface planes. Since the device essentially operates by performing linear translations in surface planes, it is suited to automation, simple, maintenance-friendly and inexpensive.

11 Claims, 10 Drawing Sheets

AUTOMATIC FIBRE TESTING SYSTEM

TECHNICAL FIELD

The present invention relates to automatic fiber testing. More particularly, the invention relates to a device for the preparation of essentially fibrous material to be tested, a device for preparing a partition of essentially fibrous material in a fibre testing system, a device for the clamping of essentially fibrous material, and a method for preparing essentially fibrous material for testing.

BACKGROUND OF THE INVENTION

When processing natural fibers, especially cotton, the quality assurance is one of the most important points. By constant monitoring of the fed raw product by means of samples taken at random it must he guaranteed that the demanded quality can be kept and that no problems occur during the processing.

The quality and the market value of the fibers are determined by means of quality factors such as length, length uniformity, strength, elongation, trash, color, micronaire and fineness. In order to automatize the standardized tests developed for this purpose different efforts have been made. The preparation of the test material was however normally carried out by hand or in at least partly automatized manner.

The preparation of the fibers to be tested contains different stages. First a certain amount of fibers must be extracted from the supplied raw fibers. Then the fibers are mostly first subjected to an optical test in which the proportion of foreign matter and the color are determined.

In order to test the distribution of lengths of fibers and the tensile characteristics such as strength, elongation and related properties, the fibers must be gripped mechanically and ordered or arranged respectively. In this context the words "carding" and "combing" are used. Carding is the opening of the fiber balls and rough arrangement of the fibers. Combing is the bringing of the fibers into the definitive parallel position. The most common method for extracting fibers, which can be found partly as different variants to be operated purely manually and partly as automatized variants, always bases on a drum with a perforated surface, whereby the perforations are on the outside of the circumference of the drum. The balls of fibers are filled into these drums and then pressed against the perforated surface from the inside by means of a mechanical device such that part of the balls of fibers protrudes through the holes on the outside. By means of a device arranged concentrically to the periphery of the drum and movably along the surface a certain amount of fibers can then be extracted from the balls and gripped by a clamp. These preparations are usually carried out manually.

An attempt at automation was made in U.S. Pat. No. 5,178,007. With this arrangement it is however obvious that the originally manually operated apparatuses were substantially copied, combined on a platform and automatized. The mechanical processes in the preparation of the fibers, which in the manual preparation mainly base on rotation movements, are unfit for automation. No effort was made to optimize the processes and make them meet the requirements of automation. A testing machine was to be constructed to be as simple and as precise as possible in order for there to be no loss in the reproducibility of the test results. The automatized solutions such as e.g. the apparatus described in U.S. Pat. No. 5,178,007 do not comprise these very characteristics. They are usually very complex in construction due to that e.g. rotation movements were chosen instead of straight movements.

In the automation of movement processes connected in a row it is often unfavorable if the originally manually operated processes are taken over without adaptation and solely the human operator is subjected to automation. This kind of solution is generally very complex mechanically is processes favorable to a human being are not necessarily optimal for a machine. In connection with this kind of solution the term "mechanized hand" is used.

SUMMARY OF THE INVENTION

It is an object of the present invention to indicate a fibre testing system for the automatic determination of material parameters which does not have the known disadvantages. The material parameters are to be determinable with a high repeating accuracy as well as precision and in as little time as possible. The transport mechanism is to be simple, maintenance friendly and inexpensive. This object is solved by the invention defined in the patent claims.

The invention does without the movement processes not suited to automation, and with a high degree of integrated detail solutions makes an optimized testing process possible. It is characterized by its modular construction which makes a total automation of the test process and any extension of the arrangement possible. In order to guarantee a short processing time of the fibers it is important to keep the processing paths as short and as straight as possible. Detours such as unfavorable rotation movements are impeded. Instead of such detours, linear translations in surface planes are preferred.

The device for the preparation of essentially fibrous material to be tested, according to the invention, comprises means for fastening said fibrous material; means for partitioning said fibrous material; and means for clamping and separating said fibrous material. Said means for fastening, said means for partitioning and said means for clamping operate in essentially parallel surface planes. Such surface planes are favorable for simple linear translations when the material to be tested is transported from one test station to another.

The device for the preparation of a partition of essentially fibrous material in a fibre testing system according to the invention has a geometric form defining a first surface plane and a second surface plane, and has passages between said first surface plane and said second surface plane. Said first and second surface plane are essentially parallel to each other. In a preferred embodiment of the invention, the device for the preparation of a partition comprises a perforated plate.

The preparation of the fibers is revolutionized by the present invention by an extraction of fibers from a ball of fibers which is linearized and thus adapted to automation. For this purpose a device for the clamping of essentially fibrous material has been developed which combines different functions. The clamping device according to the invention comprises a combination of a plurality of separating elements and clamping elements, said clamping elements being related to said separating elements. In a preferred embodiment, the clamping elements are preferably spring elements, and the separating elements are arragned in a needle comb. By means of fiber needles fibers are extracted during a linear movement and simultaneously distributed evenly in the clamping device.

With the inventive arrangement several intermediate steps which were necessary before can be impeded or carried out in optimized manner respectively. Moreover the inventive construction from standardized machine components and drive units has the effect that it is much less costly compared to known arrangements according to the state of the art.

The method for preparing essentially fibrous material for testing, according to the invention, comprises the steps of transporting said fibrous material onto a first surface plane; fastening said fibrous material in said first surface plane, allowing said fibrous material to at least partially penetrate into a second surface plane; partitioning said fibrous material by clamping at least parts of it in said second surface plane; and transporting said clamped fibrous material from said second surface plane.

BRIEF DESCRIPTION OF THE DRAWINGS

The inventive functional principle and examples of embodiments are explained in detail in connection with the following figures.

DESCRIPTION OF THE PREFERRED EMBODIMENTS

In what follows the invention is described in connection with an example of a preferred embodiment.

Figure 1:
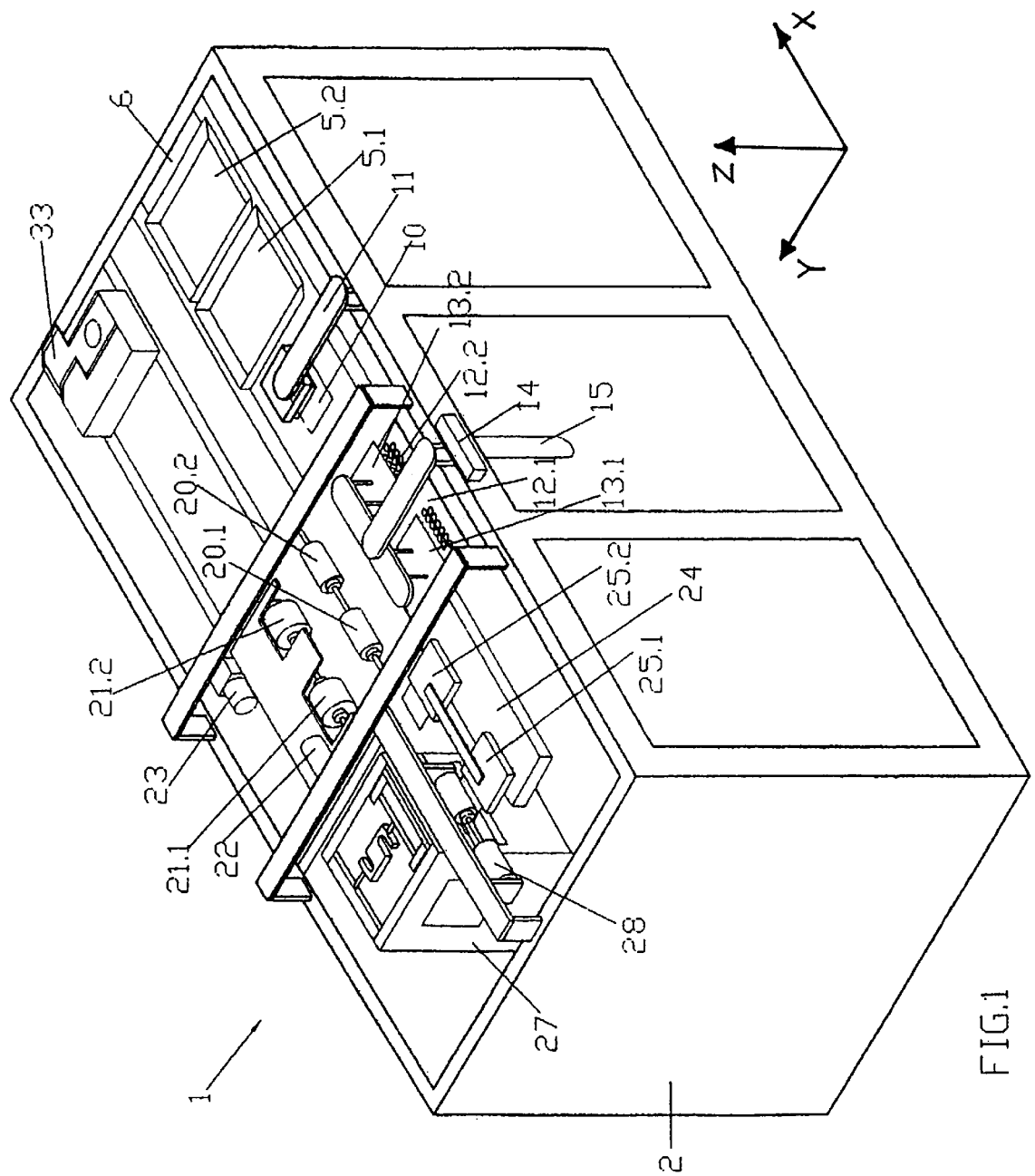
FIG. 1 shows a three-dimensional view of an automatic fiber testing facility.

FIG. 1 shows a three-dimensional total view of an automatic fiber testing system 1 according to the invention. It comprises a base plate 6 on which material to be tested (not shown in FIG. 1) is laid into a first shelf 5.1 and a second shelf 5.2. The shelves 5.1, 5.2 advantageously have a transparent base which does not obstruct the optical measuring. After the shelves 5.1, 5.2 filled with fibre balls move into position above the window 10, a sensor arm 11 presses the material to be tested against the window 10 with a defined pressing force. Below this window 10 there is a color and trash (or foreign matter) module 9 (cf. FIG. 3) which is for determination of the color and proportion of trash in the material to be tested.

The material to be tested is then transported in a linear translation onto at least one perforated plate 12.1, 12.2. These plates 12.1, 12.2, are means for partitioning the material to be tested; they serve for preparing a partition of the material to be tested. The fibrous material is then fastened to and pressed against the plates 12.1, 12.2 by means of at least one pressing plate 13.1, 13.2.

The pressing plates 13.1, 13.2 are, via a linear drive 15, fixed to a support 14. The material to be tested at least partly penetrates through the perforation of plates 12.1, 12.2 and protrudes from the lower side of the perforated plates 12.1, 12.2. By means of at least one clamping device 25.1, 25.2 (cf. FIGS. 4 and 5) arranged movably on at least one clamp support 24 which serves as a second translation means, a part of the fibers is clamped. At least part of the fibrous material is then extracted and separated from the material protruding from the perforated plates 12.1, 12.2 by moving the clamping devices 25.1, 25.2 parallel to the lower sides of perforated plates 12.1, 12.2. After a completed extraction the clamping devices 25.1, 25.2 close and fix the extracted fibers. Then the extracted fibers are combed by means of at least one combing roll 20.1, 20.2 and brushed by means of at least one brush roll 21.1, 21.2 such that a clean fiber heard is formed which is suitable for the following tests in a length and strength module 27. After completion of the test the remaining fibers which are still in the clamping device 25.1, 25.2 are removed by means of a cleaning unit 28. The fibre testing system is mounted on a base 2.

Figure 2:
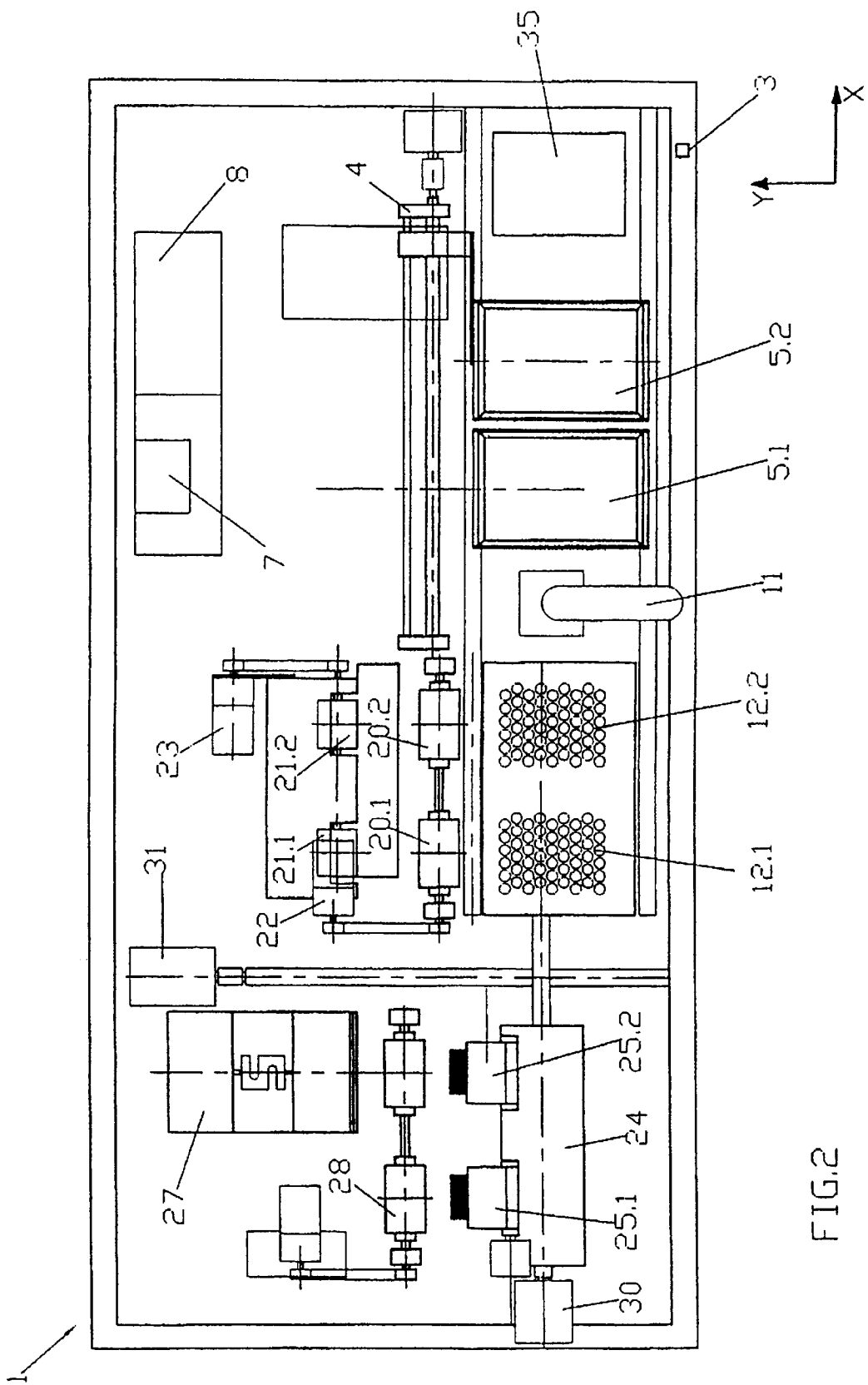
FIG. 2 shows a diagrammatic top view of a automatic fiber testing facility.

FIG. 2 shows the automatic fiber testing system of FIG. 1 in a diagrammatic top view. Besides the elements described with reference to FIG. 1, a Personal Computer (PC) 7 and, an Intelligent Process Sequencer (IPS) 8 can be seen. The Personal Computer 7 is for registering and evaluation of the measured data. The Intelligent Process Sequencer 8 is favorably used for controlling the test arrangement. Linear drives 30 and 31 are for the spatial positioning of the clamp devices 25.1, 25.2 mounted to clamp supports 24. A bar code scanner 35 is for identifying the test material. A main switch 3 for the device can be seen.

Figure 3:
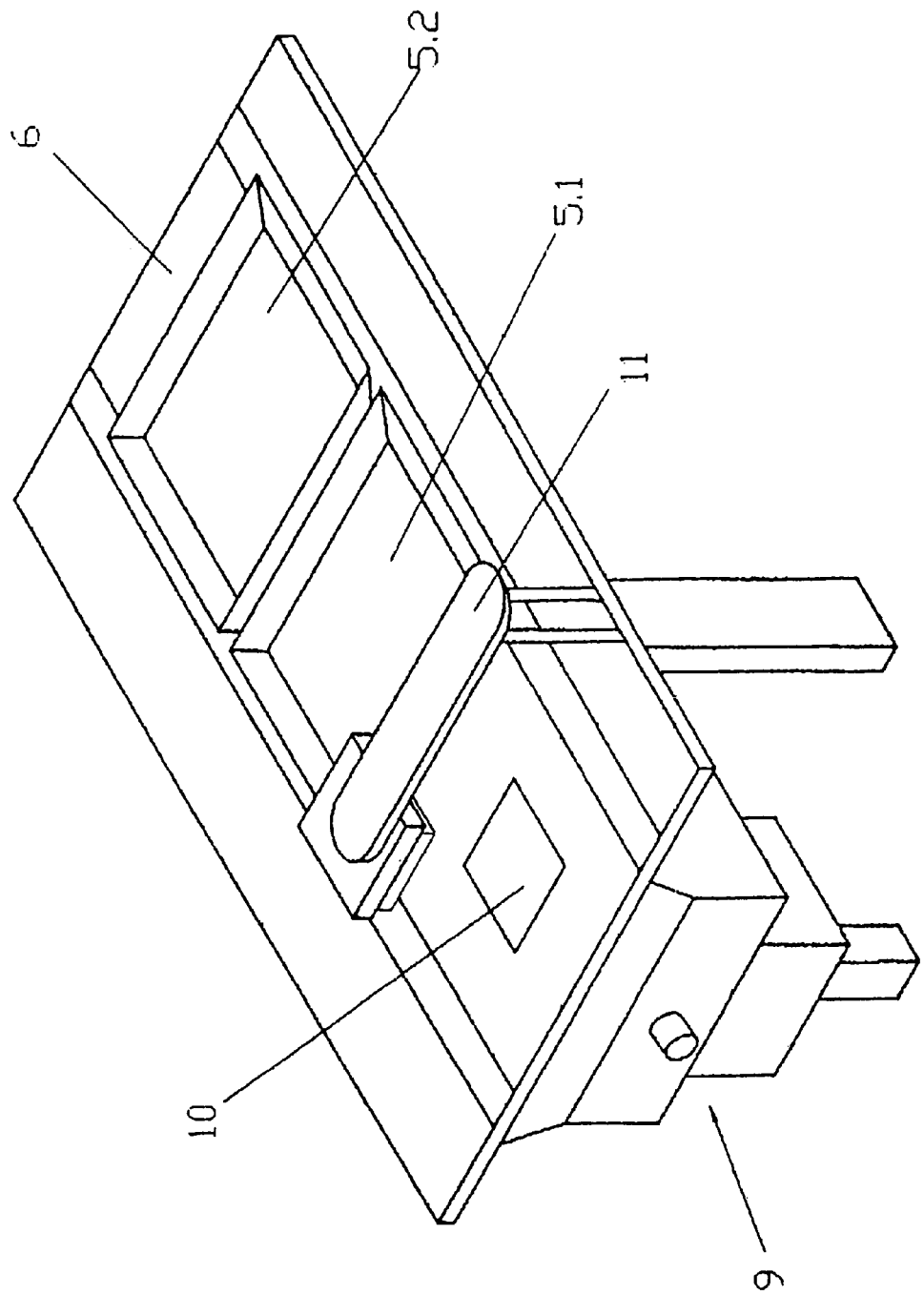
FIG. 3 shows a three-dimensional view of the color and foreign matter module.

FIG. 3 shows a color and trash module 9 with sensor arm 11 and window 10 which is favorably integrated into base plate 6. Under the transparent window 10 optical sensors (not shown) are situated.

Figure 4:
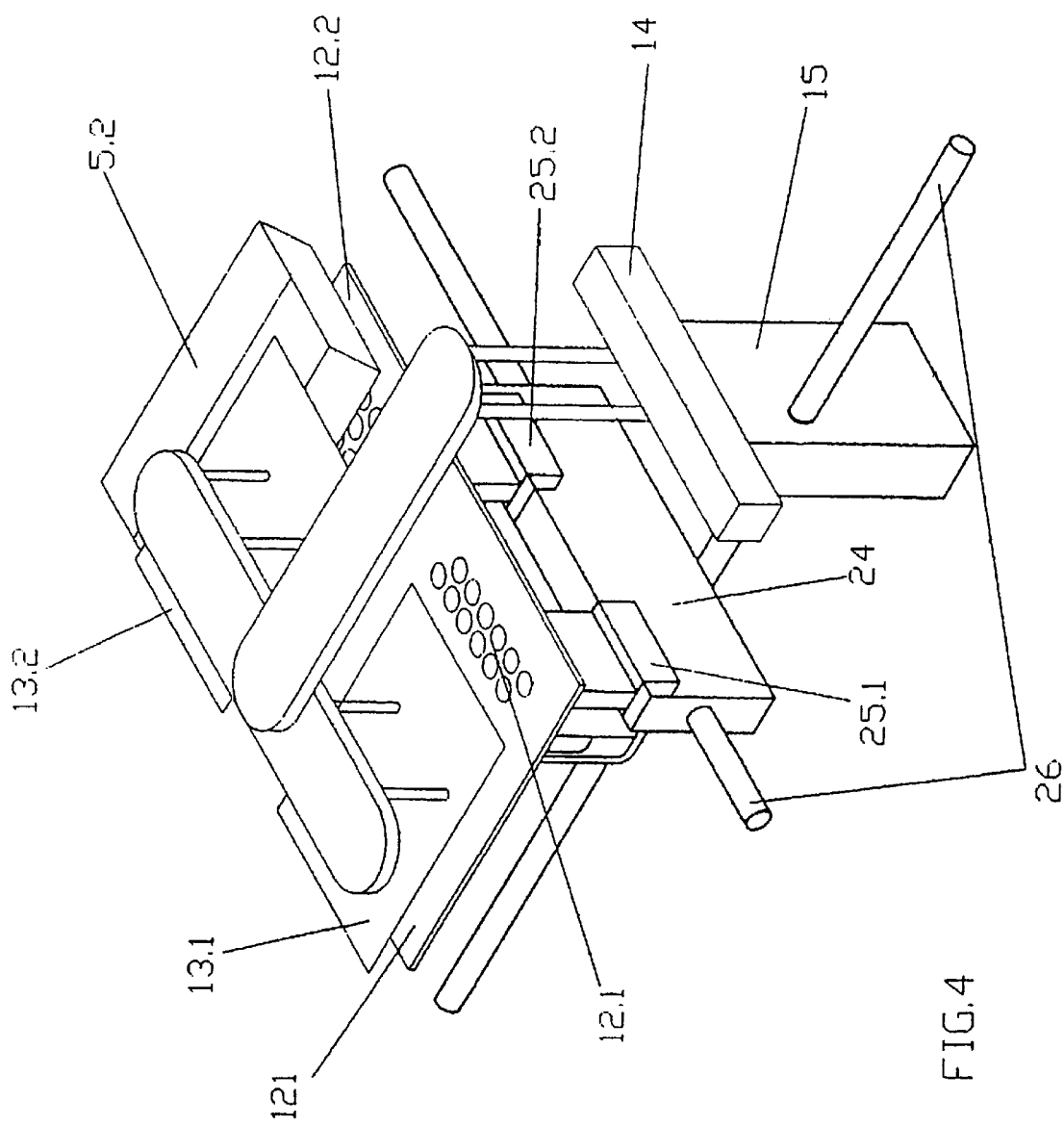
FIG. 4 shows a three-dimensional view of a fiber extraction facility in an oblique top view.

FIG. 4 shows perforated plates 12.1, 12.2 with a shelf 5.2 and pressing plates 13.1, 13.2 in a detailed view. The upper side of the perforated plates 12.1, 12.2 defines a first surface plane i21 which serves for positioning the material to be tested. Underneath perforated plates 12.1, 12.2 an X/Y-positioning-mechanism 26 can be seen which is for positioning of the clamp support 24 and the clamping device 25 fitted to it. Pressing plates 13.1, 13.2 are moved by means of linear drive 15 which is fitted to support 14.2.

Figure 5:
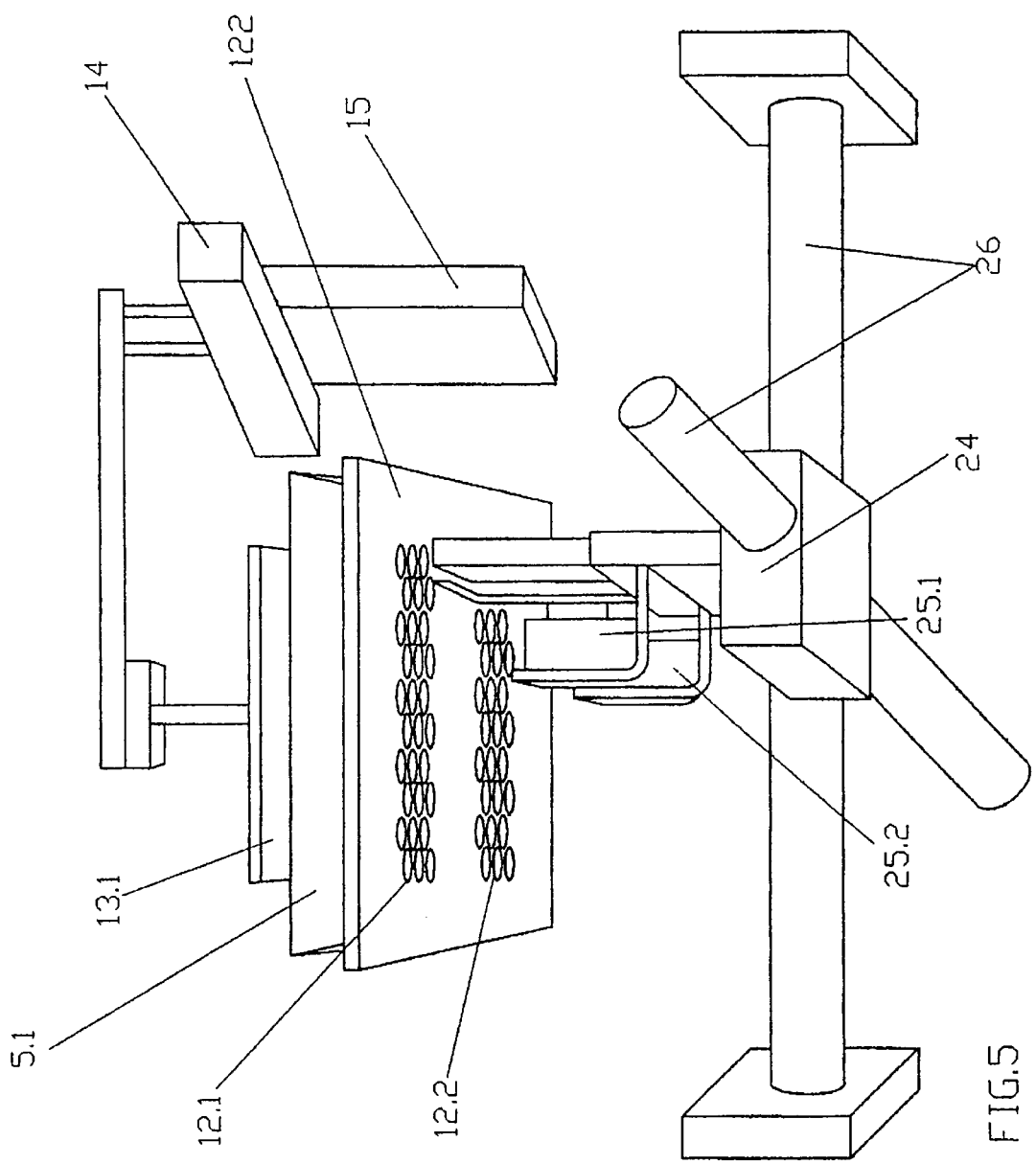
FIG. 5 shows a three-dimensional view of a perforated plate with two clamping devices.

FIG. 5 shows the same arrangement as FIG. 4 viewed from an oblique lower position. The lower side of the perforated plates 12.1, 12.2 defines a second surface plane 122 essentially parallel to the first surface plane 121; the second surface plane serves for partitioning the material to be tested. Clamping devices 25.1 and 25.2 can be seen which are mounted to clamp support 24. They are in an open position ready for taking up fibers. By movement in parallel to perforated plates 12.1, 12.2 fibers are extracted from the test material which is pressed through perforated plates 12.1, 12.2 by pressing plates 13.1, 13.2.

Figure 6:
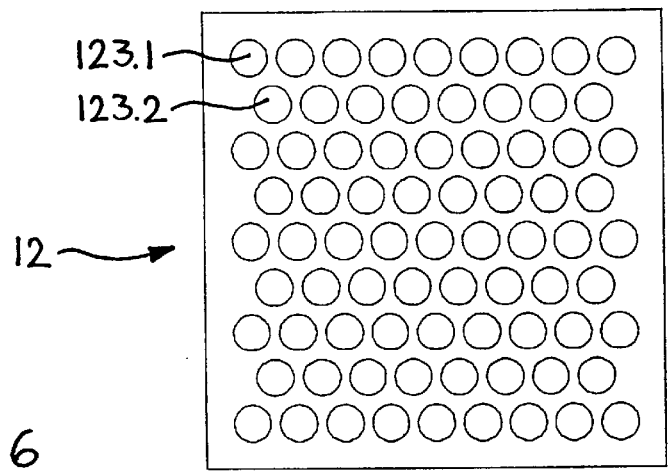
FIGS. 6–8 show top views of three different perforated plates.
Figure 7:
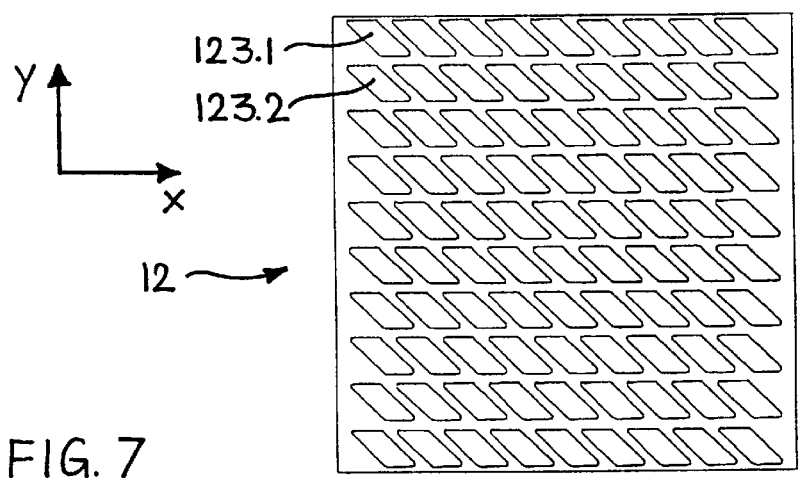
Figure 8:
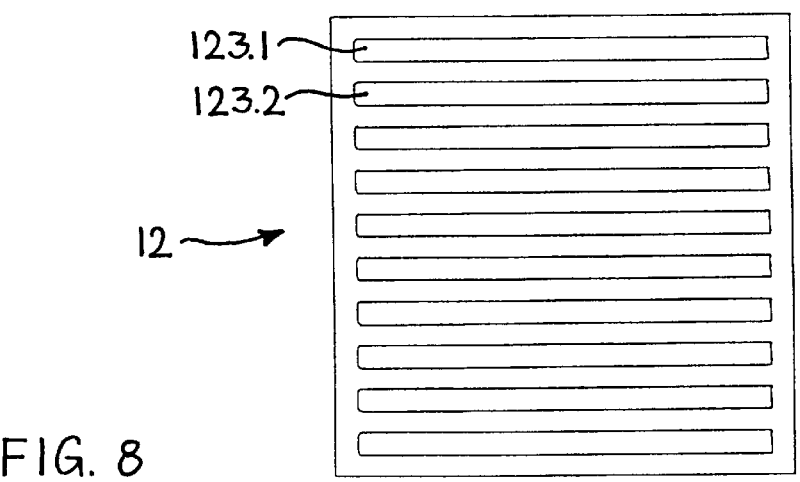

FIGS. 6–8 show top views of different perforated plates 12. The perforations or passages 123.1, 123.2, . . . may be round holes (FIG. 6), longish slits (FIG. 8) or of other shape (FIG. 7). Of course, one single perforated plate 12 can comprise different shapes of perforations 123.1, 123.2, . . . The shape and the arrangement of the perforations 123.1, 123.2 determines the characteristic features of the perforated plate 12. For example, the perforated plate 12 of FIG. 6 is isotropic with respect to the coordinates x and y, whereas the perforated plate 12 of FIG. 8 is highly anisotropic.

Figure 9:
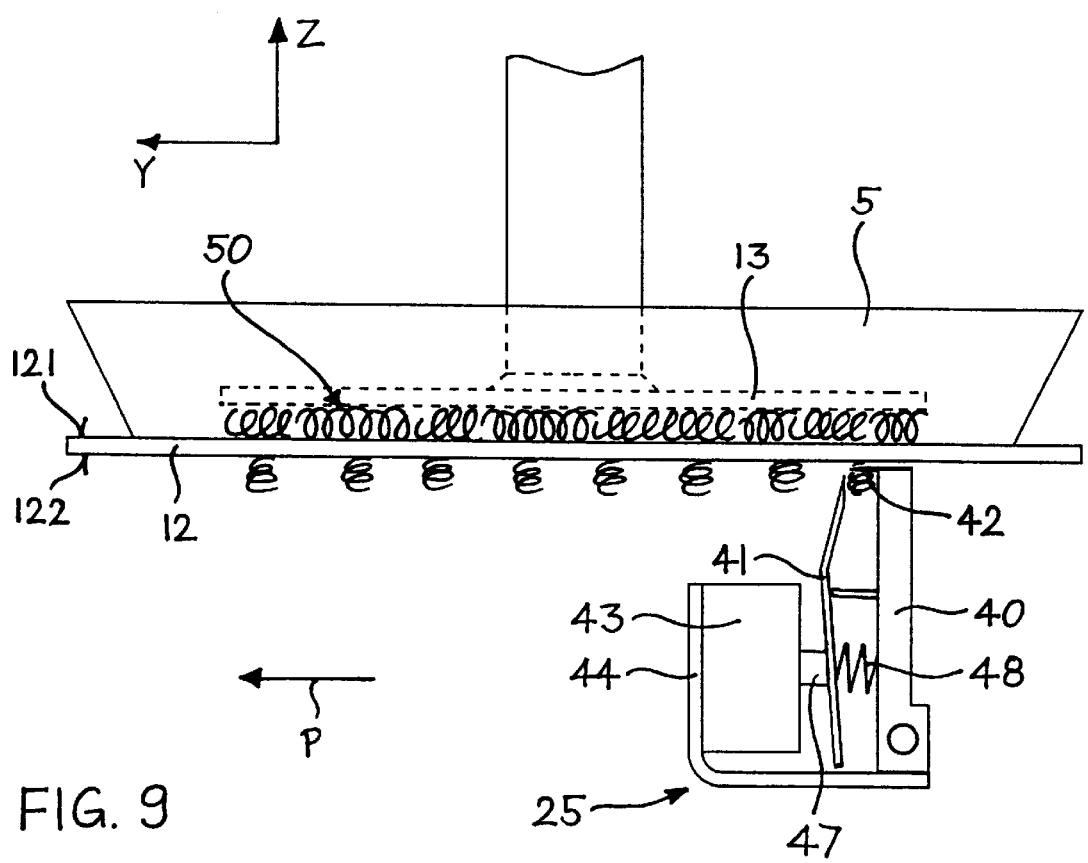
FIG. 9 shows a side view of a perforated plate with a clamping device.

FIG. 9 shows a side view of the perforated plate 12, the shelf 5, the pressing plate 13 in the shelf and the clamping device 25 consisting of base plate 40, spring plate 41, linear drive 43 and the support for linear drive 44. Moreover fibrous test material 50 is shown diagrammatically. Test material 50 is pressed against perforated plate 12 by pressing plate 13 such that a part of the test material is pressed out of the lower side of perforated plate 12. The clamping device 25 extracts a certain amount from these protruding fibers when moved in the direction of arrow P.

Figure 10:
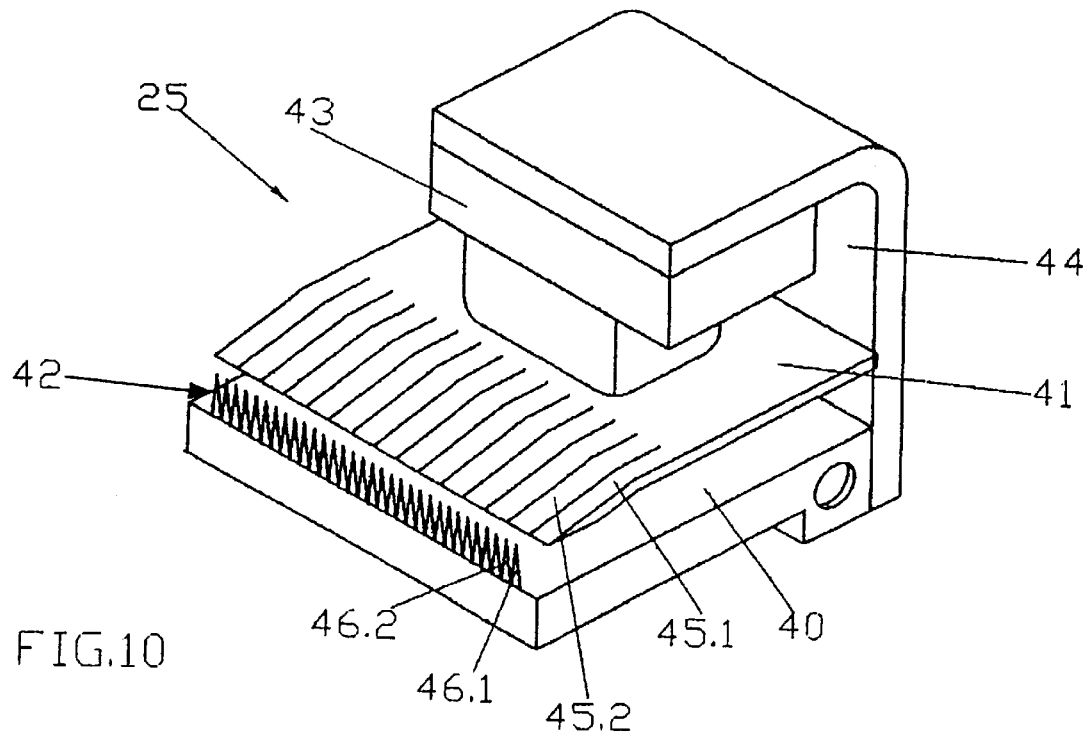
FIG. 10 shows a clamping device in opened condition.
Figure 11:
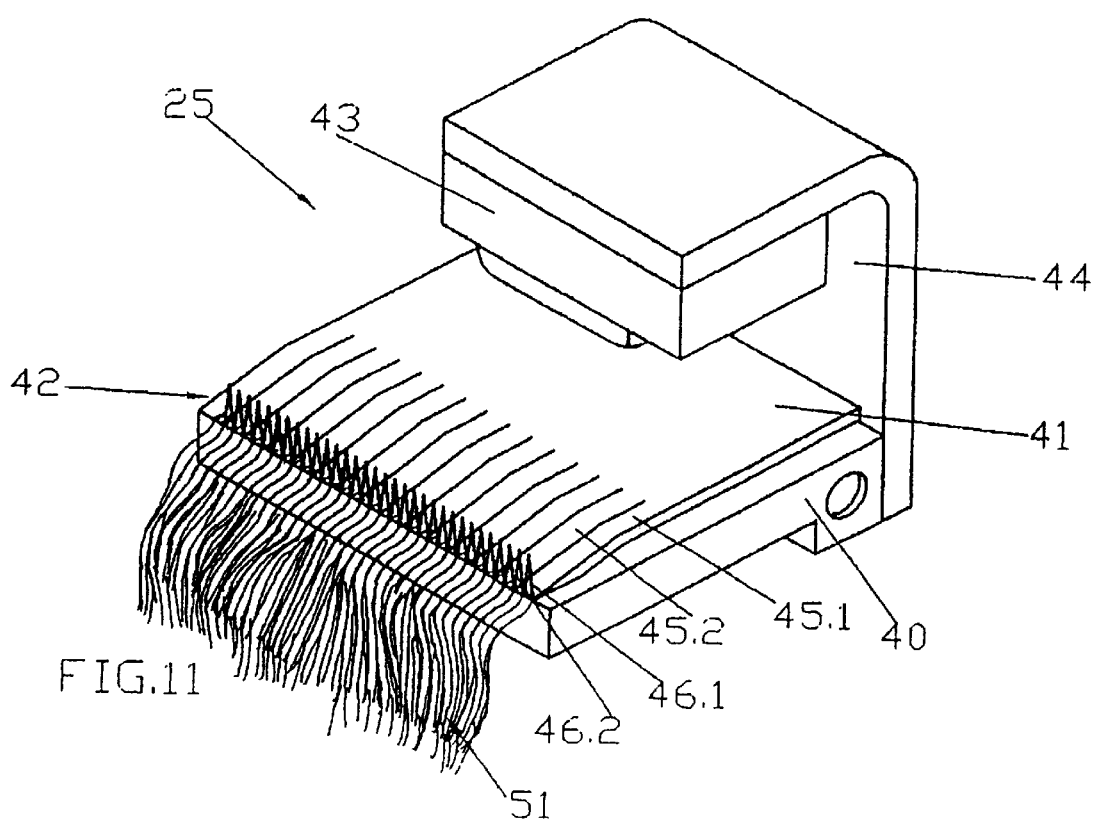
FIG. 11 shows a clamping device in closed condition with clamped fibers.

FIG. 10 shows a clamping device 25 in opened condition, FIG. 11 a clamping device 25 in closed condition. The clamping device 25 comprises a combination of a plurality of separating elements 46.1, 46.2, . . . and clamping elements 45.1, 45.2, . . . related to the separating elements 46.1, 46.2, . . . In the preferred embodiment of FIGS. 10 and 11, one clamping element 45.1 is related to one separating element 46.1. The clamping elements 45.1, 45.2, . . . are, e.g., individually movable tongue-like spring elements arranged on a front edge of a spring plate 41. Therefore, sufficient clamping takes place even if the base plate 40 and the spring plate 41 are not exactly parallel to each other. The separating elements 46.1, 46.2, . . . are arranged in a needle comb 42 on a base plate 40. Driving means 43, e.g., a linear drive, and a support 44 for the driving means 43 can he seen. The driving means 43 move, e.g., the spring plate 41 or its rear edge up and down. Between the base plate 40 and the spring plate 41 there may be provided separating means 47 (cf. FIG. 9) which act as an axis for lever movements of the spring plate 41. Between the plates 40, 41 there may also be spring means 48 (cf. FIG. 9) which press the rear edges of the plates 40, 41 from each other. FIG. 11 also shows diagrammatically extracted, carded and combed fibers 51.

The separating elements 46.1, 46.2, . . . cause an essentially uniform distribution of the fibers 51 along the front edge of the clamping device 25, since only a limited amount of fibers 51 can be inserted between two separating elements 46.1, 4 6.2. A uniform distribution of the fibers 51 is important for the subsequent fiber testing. Each clamping element 45.1, 45.2 . . . individually clamps the fibers separated by its related separating elements 46.1, 46.2, . . . The clamping force of a clamping element 45.1 and the distance between a clamping element 45.1 and the base plate 40 in the closed condition of FIG. 11 may vary from one clamping element 45.1 to another clamping element 45.2.

In the following the detailed course of one test in a device according to FIGS. 1–9 is described more closely. In a substructure 2 of the inventive automatic fiber testing system 1 (cf. FIG. 1) the different test modules test modules, e.g. 27, are arranged. In a first step a supplied but still packed fiber sample containing fibers to be tested is identified by means of a bar code scanner 35 (cf. FIG. 2). Then the sample is opened and spread out on several, preferably two shelves 5.1, 5.2. The shelves 5.1, 5.2 each comprise an opening in their bases such that the fibers to he tested come to lie on a base plate 6. The amount of testing material should be sufficient to fill the shelves 5.1, 5.2 totally and cover at least one window 10 which is normally situated in base plate 6.

After completion of the preparations the test process is started by operation of a master control 3 (cf. FIG. 2). The Intelligent Process Sequencer (IPS) equipped with a logic which is advantageously controlled by a Personal Computer 7 controls the course of the test. On receiving a corresponding command, e.g. "Start Test" the IPS 8 starts its work.

First it is tested whether any testing material is available (here on the shelves 5.1, 5.2). This can advantageously happen by means of optical sensors such as they are also e.g. used for photoelectric barriers. These sensors have the possibility to register the chosen region and to check whether sufficient test material is available. Of course the resolution of this arrangement can be increased and adapted by increase of the amount of sensors. Especially corresponding other sensors can be used.

When the material to be tested has been registered a sensor arm 11 is activated which is advantageously located above window 10. This arm 11 is now positioned above the material to be measured and then lowered towards it until it touches it and presses it against window 10, whereby it is advantageous to the quality of the test if a defined pressing force is used here. As however the testing material is never of exactly the same amount it is useful for sensor arm 11 to be combined with a force sensing device which monitors the mechanical pressing force and keeps it constant according to a predetermined value. Below window 10 the color and trash module 9 is situated (cf. FIG. 3). The quality of the color is tested by means of color and trash module 9, advantageously by directing light from a light source onto the material to be measured. The rays reflected by the material to be measured are registered by means of suitable sensors e.g. photographic sensors or CCD-arrays such as are used in video cameras. The measured results are then fed into a Received Radiation Processor (RRP) and analyzed. The characterizing of the quality of color of the measured material is carried out by the Intelligent Process Sequencer (IPS) 8. With the arrangement disclosed here it is obviously, if desired, also possible to analyze other recordable parameters such as specific gravity, density per length unit or thickness of fiber.

The Received Radiation Processor (RRP) in the arrangement shown here works under the guidance of the Intelligent Process Sequencer (IPS) 8 or can even he combined to this; it is however also possible that it carries out functions autonomously. The second function which is fulfilled by this arrangement is, in the arrangement shown here, the determination of the composition of the material to he measured. For this task it is advantageous to use at least one electronic camera which registers the radiation reflected by the material to be measured. This task can, due to the inventive design of the testing device, be carried out simultaneously with the measurement of color. The measurement of color can, of course, if desired, also be looked after by the same arrangement, e.g. an electronic camera.

After completion of this first measurement the first shelf 5.1 is shifted by one distance such that the following second shelf 5.2 with material to be measured is positioned in the region of effect of sensor arm 11. With the second shelf 5.2 the substantially same tests are carried out as with the first shelf 5.1 by which it is achieved that the accuracy and the quality of the test results are increased. In order to, if desired, improve the optical tests described first here several measuring heads are arranged in parallel can be used. The carrying out of the optical test generally does not require very much time such that for reasons of cost it is hardly worthwhile to realize a parallel processing.

The shelves 5.1, 5.2 with the material 50 to be measured are advantageously positioned by means of linear drives. An increase of the accuracy can be achieved by additional sensors.

A substantial idea is that the shelves 5.1, 5.2 are not subject to fixed guidance and thus can also be guided in other directions when the order of the tests changes. Thus it is, among other things, possible to guarantee a modular structure of the test arrangement which allows a continuous extension of the system and the carried out tests. Due to the modularity and especially to the not rigid movement processes the track of shelves 5.1, 5.2 can be extended to any length and in any direction, similarly to the track of a model railway.

In the arrangement shown here the density ("micronaire") test is carried out in a micronaire tester 33 in parallel to the test of the color quality and composition. For this purpose a defined amount of fibers is brought into the test module and lead through.

After testing of the fibers by means of the color and trash module 9, shelves 5.1, 5.2 are shifted further on base plate 6 by means of linear drive 4 until they come to lie above perforated plates 12.1, 12.2. Above these perforated plates 12.1, 12.2 and shelves 5.1, 5.2 there are pressing plates 13.1, 13.2 which can be moved by means of a linear drive 15. This linear drive 15 and the pressing plates 13.1, 13.2 connected to it are fixed to a support 14 which is supported on substructure 2.

Pressing plates 13.1, 13.2 are lowered onto the material to be measured by means of linear drive 15 and press it against perforated plates 12.1, 12.2 with a defined force such that the material to be measured is pressed out of the lower side of perforated plates 12.1, 12.2 up to a defined degree. Clamping devices 25.1, 25.2 which were positioned below the perforated plates 12.1, 12.2 in an opened position are then moved along perforated plates 12.1, 12.2 in the direction of arrow P (cf. FIG. 9). Thus the clamping devices 25.1, 25.2 extract fibers from the material pressed through perforated plates 12.1, 12.2. At the end of the perforated plates 12.1, 12.2, when all the material to be tested has been scanned through, the beard clamps close due to the spring plate 41 being pressed against base plate 40 by driving means 43. The fibers 51 are thus fixed fast.

In a next step the fibers fixed in the clamping devices 25.1, 25.2 are combed by means of at least one combing roll 20.1, 20.2 (cf. FIG. 1) and brushed by means of at least one brush roll 21.1, 21.2. For this purpose, the clamping devices 25.1, 25.2 are translated in y direction and rotated by 90° about the x axes. Combing rolls 20.1. 20.2 are advantageously driven by means of an electric motor 22 and the brush rolls 21.1, 21.2 are advantageously driven by means of an electric motor 23. The fibers thus prepared and held by the clamping devices 25.1, 25.2 are then examined concerning their mechanical characteristics in length and strength module 27. For this purpose, a translation in the x direction of the clamping devices 25.1, 25.2 takes place. After examination of the mechanical characteristics, clamping devices 25.1, 25.2 are opened and the remaining fibers removed by means of cleaning unit 28.

Figure 12:
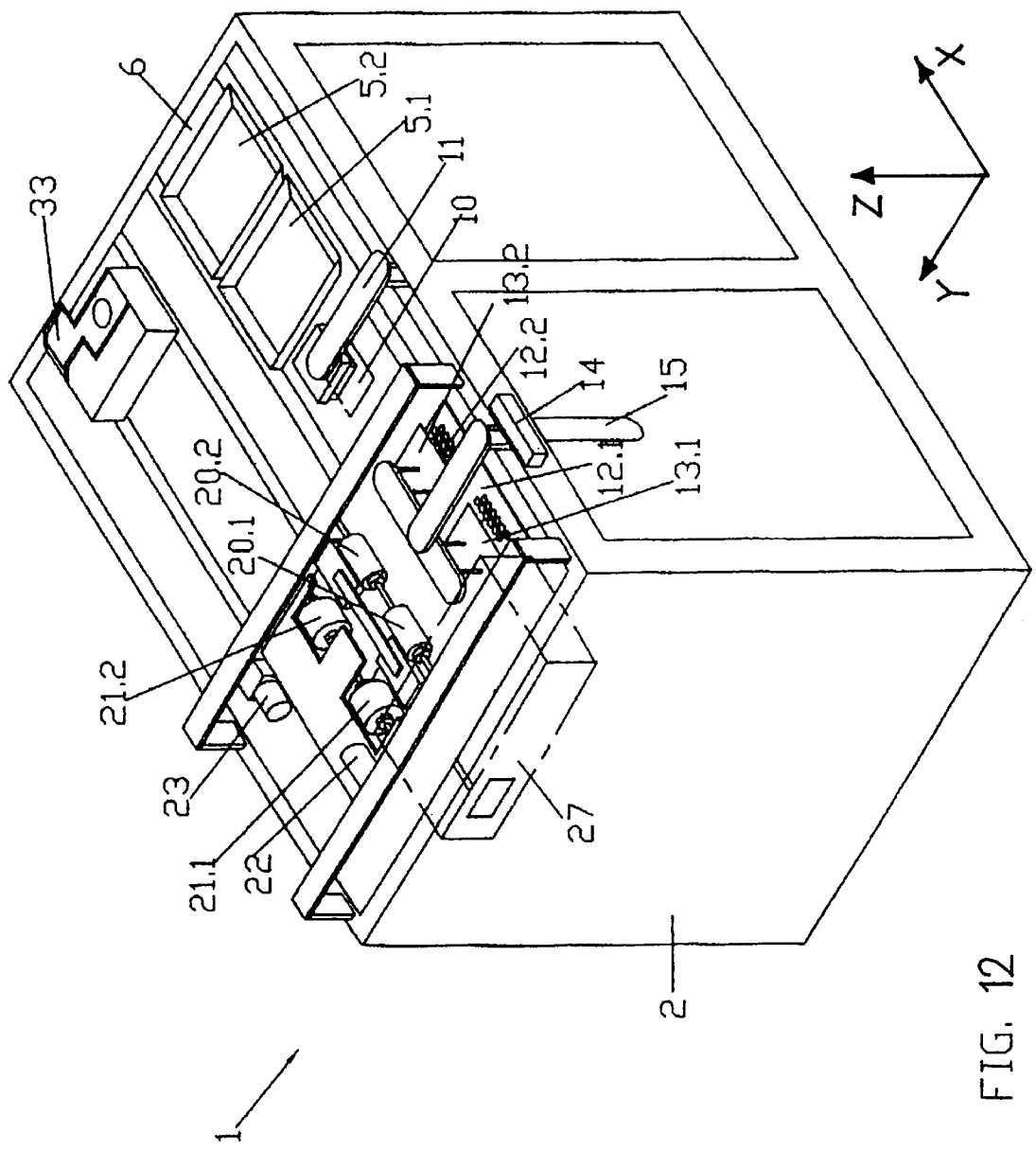
FIG. 12 shows a three-dimensional view of a further embodiment of an automatic fiber testing facility.
Figure 13:
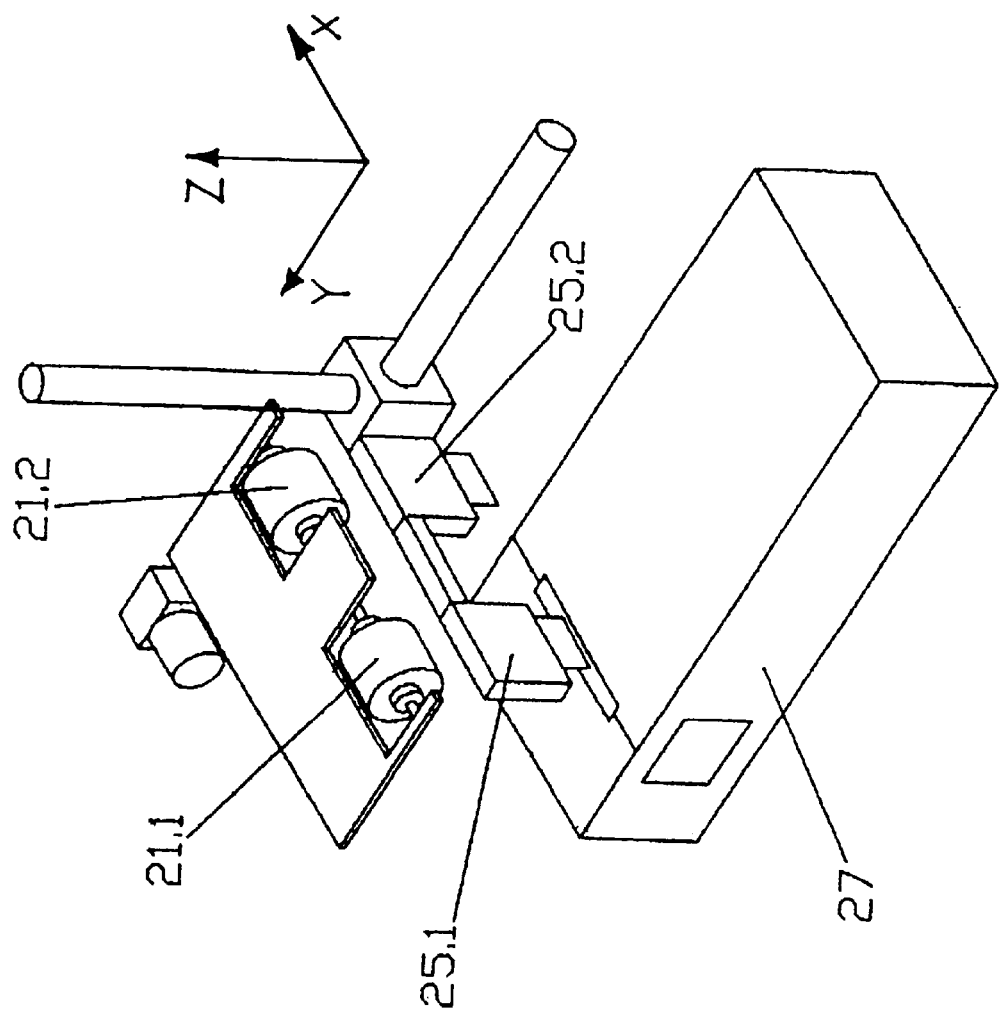
FIG. 13 shows a three-dimensional view of a detail of the embodiment according to FIG. 12.

FIG. 12 shows an embodiment of the device 1 according to the invention which in some points differs from the embodiment of FIGS. 1–9; FIG. 13 shows a details of the embodiment of FIG. 12. In this embodiment, the length and strength module 27 is arranged beneath the brush rolls 21.1, 21.2, and the side of the length and strength module 27 which in the embodiment of FIGS. 1–9 lies in the xz plane is in the embodiment of FIG. 12 facing the brush rolls 21.1, 21.2. After brushing operation performed by the brush rolls 21.1, 21.2, instead of moving in the x direction for length and strength measurement, the clamping devices 25.1, 25.2 are rotated by 90° C. about the x axes to face the length and strength module 27 and are moved in the z direction (cf. FIG. 13) for length and strength measurement. An advantage of the embodiment of FIGS. 12 and 13 is a volume and space reduction of the device 1.

We claim:

1. A device for the preparation of essentially fibrous raw material to be tested, comprising means for fastening said fibrous material;

means for partitioning said fibrous material; and means for clamping and separating said fibrous material;

said means for fastening, said means for partitioning and said means for clamping operating in essentially flat parallel surface planes.

2. A device according to claim 1 wherein said means for fastening said fibrous material comprise a pressing plate.

3. A device for the preparation of a partition of essentially fibrous raw material in a fibre testing system, said device having a geometric form defining a first surface plane and a second surface plane and having passages between said first surface plane and said second surface plane, said first and second surface planes being essentially flat and parallel to each other.

4. A device according to claim 3 wherein said first surface plane serves for positioning said fibrous material moved onto said first surface plane and said second surface plane serves for partitioning said fibrous material through said passages by second translation means.

5. A device according to claim 3 wherein said device comprises a perforated plate.

6. A device for the clamping of essentially fibrous raw material, comprising a combination of a plurality of adjacently disposed and spaced apart separating elements extending from a support member and individual resilient clamping elements, said clamping elements being related to said separating elements so that upon said clamping elements being moved to a clamping position adjacent said support member, said individual clamping elements resiliently clamp fibers caught between said separating elements against said support member.

7. A device according to claim 6 wherein one clamping element is related to each separating element.

8. A device according to claim 6 wherein said clamping elements are arranged on a plate.

9. A device according to claim 6 wherein said clamping elements are spring elements.

10. A device according to claim 6 wherein said separating elements are arranged in a needle comb.

11. A method for preparing essentially fibrous raw material for testing, comprising the steps of transporting said fibrous material onto a first surface plane;

fastening said fibrous material in said first surface plane, allowing said fibrous material to at least partially penetrate into a second surface plane;

partitioning said fibrous material by clamping at least parts of it in said second surface plane; and transporting said clamped fibrous material from said second surface plane.

* * * * *